United States Patent [19]

Jessel, Jr. et al.

[11] Plant 4,272

[45] Jun. 27, 1978

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 835,829

[22] Filed: Sep. 22, 1977

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Beall & Jeffery

[57] ABSTRACT

A daisy capitulum type of chrysanthemum plant which is a sport of the cultivar Sophisticate, disclosed in U.S. Plant Pat. No. 3,944, and which is distinguished from the parent cultivar by its medium yellow ray floret color.

1 Drawing Figure

The present invention comprises a new and distinct cultivar of *Chrysanthemum morifolium,* Ramat., hereinafter referred to by the cultivar name Yellow Sophisticate (#70009F08).

Yellow Sophisticate is a product of planned sport induction program which had the objective of expanding the color range of the parental cultivar, Sophisticate (#70009008; U.S. Plant Pat. No. 3,944).

Yellow Sophisticate was discovered and selected by William E. Duffett and Walter H. Jessel, Jr. on Aug. 10, 1976 as one plant within a flowering block of Sophisticate in a controlled environment in Barberton, Ohio. Plants within the flowering block were derived from stock plants which had been irradiated as root cuttings with an x-ray source of 1800 r units.

The first act of asexual reproduction of Yellow Sophisticate was accomplished when vegetative cuttings were taken from the initial selection in February, 1977 in a controlled environment in Barberton, Ohio by a technician working under formulations established and supervised by Walter H. Jessel, Jr. and William E. Duffett. Horticultural examination of selected units initiated Aug. 10, 1976 has demonstrated that the combination of characteristics as herein disclosed for Yellow Sophisticate are firmly fixed and are retained through successive generations of asexual reproduction.

Yellow Sophisticate has not been observed under all possible environmental conditions. The phenotype may vary significantly with variations in environment such as temperature, light intensity and daylength. The following observations, measurements, and comparisons describe plants grown in Barberton, Ohio under greenhouse environmental conditions which approximate those generally used in commercial practice, as described in Chart A which appears at the end of the present specification. A light intensity chart of general use is shown in ASHAE Trans., Vol. 64, page 64, and reference is made thereto.

The following traits have been repeatedly observed and are determined to be basic characteristics of Yellow Sophisticate which in combination distinguish this chrysanthemum as a new and distinct cultivar:

1. Daisy capitulum type.
2. Flat capitulum form.
3. Medium yellow ray floret color.
4. Yellow-green (immature) to yellow (mature) disc floret color.

5. Diameter across face of capitulum from 85 to 90 mm. at maturity.
6. Uniform nine week flowering response to photoperiodic short-day control.
7. Medium plant height (requires 1–2 long day weeks prior to short days to obtain a flowered plant height of 72 to 82 cm. when grown as a single stem plant for May through October flowerings).
8. Semi-spreading branching pattern.
9. Minimal pollen development.

The accompanying color photographic drawing shows typical inflorescence and foliage characteristics of Yellow Sophisticate. Color representations are as nearly true as possible with illustrations of this type.

Of the many commercial cultivars known to the present inventors, the most similar existing cultivar in comparison to Yellow Sophisticate is the parental cultivar, Sophisticate, disclosed in our issued U.S. Plant Pat. No. 3,944, granted Aug. 24, 1976. Reference is made to attached Chart B which compares certain characteristics of Sophisticate with the same characteristics of Yellow Sophisticate. As noted in Chart B, the primary distinguishing characteristic of Yellow Sophisticate in comparison to Sophisticate is that of ray floret color. All other characteristics of Yellow Sophisticate are similar to those same characteristics of Sophisticate.

In the following description, color references are made to The Munsell Limit Color Cascade, 1972 edition. The color values were determined between 4:30 and 5:00 P.M. on May 25, 1977 under 150 foot-candle light intensity at Barberton, Ohio.

Botanical classification: *Chrysanthemum morifolium,* Ramat., cv Yellow Sophisticate.

INFLORESCENCE

Capitulum:
- *Form.*—Flat.
- *Type.*—Daisy.
- *Diameter across face.*—85 to 90 mm.

Corolla of ray florets:
- *Color (abaxial).*—25-5 to 25-3.
- *Color (adaxial).*—25-3 to 25-2.

Corolla of disc florets:
- *Color.*—22-8 (immature) to 26-6 (mature).

Reproductive organs:
- *Androecium.*—Present disc florets only.
- *Gynoecium.*—Present both ray and disc florets.

PLANT

General appearance: Semi-spreading branching pattern; medium height.

Foliage:

*Color (abaxial)*.—Approximately 19-15.

*Color (adaxial)*.—Approximately 19-13 to 19-14.

Sophisticate and particularly characterized as to uniqueness by the combined characteristics of daisy capitulum type; flat capitulum form; medium yellow ray floret color; yellow green (immature) to yellow (mature) disc floret color; diameter across face of capitulum from 85 to 90 mm. at maturity; uniform 9 week flowering response to photoperiodic short-day control; medium plant height; semi-spreading branching pattern; and minimal pollen development.

CHART A

AVERAGE GREENHOUSE CHRYSANTHEMUM ENVIRONMENTS USED FOR BARBERTON, OHIO

| SEASON | TEMPERATURES USED Night | Bright Day | Cloudy Day | LIGHTING USED | BLACK CLOTH USED | SUPP $CO_2$ |
|---|---|---|---|---|---|---|
| FALL | 65° F to 56° F | 65° F to 80° F | 60° F to 75° F | 2 to 4 weeks at 3 Hours Per Night of 7–10 f.c. | To Sept. 15 on - 5:30 PM Off - 7:30 AM | From Oct 15 300 ppm |
| WINTER | 58° F to 62° F | 65° F to 70° F | 60° G to 65° F | 2 to 5 weeks at 5 Hours Per Night of 7–10 f.c. | None | 300 ppm |
| SPRING | 58° F to 65° G | 65° F to 80° F | 60° F to 75° F | 2 to 4 weeks at 5 Hours Per Night of 7–10 f.c. | From Mar. 15 on - 5:30 PM Off - 7:30 AM | To Apr. 15 300 ppm |
| SUMMER | 62° F to 68° F | 70° F to 90° F | 65° F to 75° F | 1 to 2 weeks at 3 Hours Per Night of 7–10 f.c. | On - 6:00 PM Off - 8:00 AM | NONE |

CHART B

COMPARISON OF YELLOW SOPHISTICATE AND SOPHISTICATE

| CULTIVAR | RAY FLORET COLOR | DIAMETER ACROSS FACE OF CAPITULUM | PLANT HEIGHT | BRANCHING PATTERN | FLOWERING RESPONSE PERIOD | CAPITLUM FORM AND TYPE |
|---|---|---|---|---|---|---|
| Yellow Sophisticate | Medium Yellow | 85 to 90 mm. | Medium | Semi-spreading | 9 week | Flat daisy |
| Sophisticate | White | 85 to 90 mm. | Medium | Semi-spreading | 9 week | Flat daisy |

COMPARISONS MADE OF PLANTS GROWN IN A GREENHOUSE IN BARBERTON, OHIO UNDER ENVIRONMENTAL CONDITIONS AS DESCRIBED IN CHART A.

We claim:

1. A new and distinct cultivar of *Chrysanthemum morifolium;* Ramat, known by the cultivar name Yellow

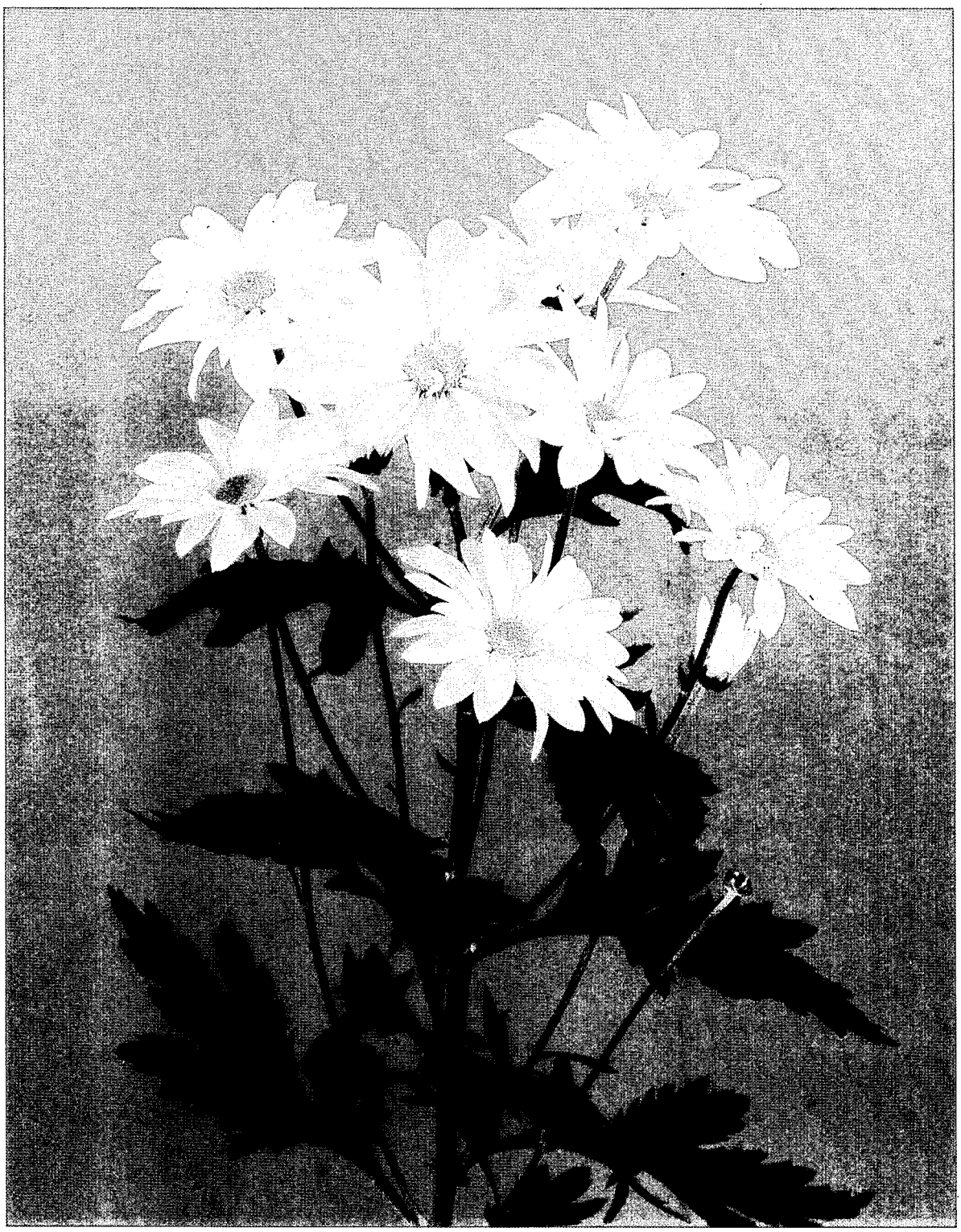

* * * * *